United States Patent
Hoover et al.

(10) Patent No.: US 9,524,376 B2
(45) Date of Patent: Dec. 20, 2016

(54) APPARATUS, SYSTEM, AND METHOD FOR PERSONALIZED MEDICATION LABELS

(71) Applicant: Xerox Corporation, Norwalk, CT (US)

(72) Inventors: Linn C. Hoover, Webster, NY (US); William J. Hannaway, Webster, NY (US); William J. Nowak, Webster, NY (US); Zhigang Fan, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 196 days.

(21) Appl. No.: 14/192,285

(22) Filed: Feb. 27, 2014

(65) Prior Publication Data
US 2015/0242713 A1 Aug. 27, 2015

(51) Int. Cl.
G06F 19/00 (2011.01)
G06F 3/12 (2006.01)

(52) U.S. Cl.
CPC ......... *G06F 19/3456* (2013.01); *G06F 3/1203* (2013.01); *G06F 3/1243* (2013.01); *G06F 3/1256* (2013.01)

(58) Field of Classification Search
None
See application file for complete search history.

(56) References Cited

U.S. PATENT DOCUMENTS

| | | | |
|---|---|---|---|
| 5,852,590 A * | 12/1998 | de la Huerga | A61J 7/0481 368/10 |
| 8,384,517 B2 * | 2/2013 | Chu | G06K 17/0022 340/5.91 |
| 8,391,104 B2 * | 3/2013 | de la Huerga | A61J 1/035 206/459.5 |
| 2003/0189732 A1 * | 10/2003 | Bean | A61J 1/03 358/302 |
| 2005/0038558 A1 * | 2/2005 | Keene | G06F 19/3456 700/235 |
| 2006/0158739 A1 * | 7/2006 | Raymond | B44F 1/06 359/619 |
| 2010/0133139 A1 * | 6/2010 | Lowe | B65D 83/04 206/534 |

(Continued)

OTHER PUBLICATIONS

U.S. Appl. No. 13/892,865, filed May 13, 2013, Unpublished, Kikami, et al.

*Primary Examiner* — Nicholas Pachol
*Assistant Examiner* — Pawandeep Dhingra
(74) *Attorney, Agent, or Firm* — Simpson & Simpson, PLLC (57) ABSTRACT

A computer-based apparatus for labeling medications, including: a processor for a computer configured to: calculate a configuration of a first medication package using a first digital image of the first medication package; create, using the configuration, a package template; receive first prescription information including a name of a patient, a name of a medication, a dosage of the medication, an amount of the medication, and a schedule for taking the medication; create a first custom label, using the package template and the first prescription information, the first custom label including a first plurality of data fields including the first prescription information and a configuration for the first custom label; and transmit first data, including the first custom label with the first prescription information entered in the first plurality of data fields, to a printer.

39 Claims, 10 Drawing Sheets

(56) References Cited

U.S. PATENT DOCUMENTS

| | | | |
|---|---|---|---|
| 2010/0241446 A1* | 9/2010 | Eckert | G06Q 50/22 705/2 |
| 2011/0240729 A1* | 10/2011 | Schuck | G06F 19/3487 235/375 |
| 2012/0000592 A1* | 1/2012 | Mase | G09F 3/02 156/60 |
| 2012/0004770 A1* | 1/2012 | Ooyen | B65C 1/026 700/235 |
| 2013/0117044 A1* | 5/2013 | Kalamas | G06Q 50/24 705/3 |
| 2013/0327822 A1* | 12/2013 | Keefe | G06F 17/40 235/375 |
| 2014/0081649 A1* | 3/2014 | Langdon | A61J 1/14 705/2 |
| 2014/0257843 A1* | 9/2014 | Adler | G09F 3/0289 705/2 |
| 2014/0282197 A1* | 9/2014 | Keefe | G06F 19/326 715/771 |
| 2014/0307269 A1* | 10/2014 | Hirabayashi | G06K 15/025 358/1.6 |
| 2014/0353196 A1* | 12/2014 | Key | G09F 3/0288 206/459.1 |
| 2015/0102100 A1* | 4/2015 | Hattrup | G06Q 50/28 235/375 |
| 2015/0156342 A1* | 6/2015 | Fries | H04N 1/00103 358/1.15 |
| 2015/0231896 A1* | 8/2015 | Hattrup | B41J 3/407 493/320 |

* cited by examiner

APPARATUS, SYSTEM, AND METHOD FOR PERSONALIZED MEDICATION LABELS

TECHNICAL FIELD

The present disclosure relates to an apparatus, system, and method for using a digital image of a medication package to create a label template for a label. The template includes data fields for information related to a medication and a patient and the label has a size commensurate with the medication package.

BACKGROUND

Medication adherence, including patient adherence to medication regimens, is an important aspect of any system providing medical services. Specifically, lack of medication adherence has a negative effect on outcomes and increases costs associated with providing medical services. For example, research shows that:

1. Approximately 25% of patients prescribed medications for a new illness fail to fill their initial prescription;
2. Approximately half of patients taking maintenance medications for a chronic disease stop taking their medications within the first year; and,
3. The estimated cost of unnecessary medical treatment attributable to medication non-adherence is $290 billion annually.

Further, under the applicable laws and regulations, health care providers will be not be reimbursed for patients that are readmitted for the same chronic illness, such as congestive heart failure, within 30 days. Hospital admission data from 2009 shows 1.3 million Medicare patients were readmitted within 30 days based on drug events at an estimated cost of $12 billion. Other data indicates that one cause of repeat admissions is lack of adherence to medication regimens. Many of the reasons for the lack of adherence are related to problems with labeling of prescription medications. In general, the problems are related to inflexibility in the labeling process and include: illiteracy of the patient, the language used on the medication label (English typically) is not the primary language of the patient, and the size or configuration of the label is inadequate to enable inclusion of information necessary or helpful for the patient to understand and comply with the medication regimen.

Known medication packaging distribution channels use centralized distribution centers with minimum 12-24 hour turnaround times. Health care providers in hospitals often write or change patient prescriptions the day a patient is released, which does not allow enough time to provide the prescribed medication at the time of the patient's release.

SUMMARY

According to aspects illustrated herein, there is provided a computer-based apparatus fir labeling medications, including: a processor for a computer configured to: calculate a configuration of a first medication package using a first digital image of the first medication package; create, using the configuration, a package template; receive first prescription information including a name of a patient, a name of a medication, a dosage of the medication, an amount of the medication, and a schedule for taking the medication; create a first custom label, using the package template and the first prescription information, the first custom label including a first plurality of data fields including the first prescription information and a configuration for the first custom label; and transmit first data, including the first custom label with the first prescription information entered in the first plurality of data fields, to a printer.

According to aspects illustrated herein, there is provided a computer-based system for labeling medications, including: a printer; a two-dimensional cutter; and a processor for a computer configured to: calculate a configuration of a first medication package using a first digital image of the first medication package; create, using the configuration, a package template; receive first prescription information including a name of a patient, a name of a medication, a dosage of the medication, an amount of the medication, and a schedule for taking the medication; create a first custom label, using the package template and the first prescription information, the first custom label including a first plurality of data fields including the first prescription information and a first shape and a first size for the first custom label; and transmit first data, including the first custom label with the first prescription information entered in the first plurality of data fields, to a printer. The printer is configured to print the first data on a first sheet and the two-dimensional cutter is configured to cut the first sheet to form the first custom label.

According to aspects illustrated herein, there is provided a computer-based method for labeling medications, including: calculating, using the processor, a configuration of a first medication package using a first digital image of the first medication package; creating, using the processor and the configuration, a package template; receiving, using the processor, first prescription information including a name of a patient, a name of a medication, a dosage of the medication, an amount of the medication, and a schedule for taking the medication; creating, using the processor, the package template and the first prescription information, a first custom label including a first plurality of data fields including the first prescription information and a first configuration for the first custom label; and transmitting, using the processor, first data, including the first custom label with the first prescription information entered in the first plurality of data fields, to a printer.

According to aspects illustrated herein, there is provided a computer-based method for labeling medications, including: calculating, using the processor, a configuration of a first medication package using a first digital image of the first medication package; creating, using the processor and the configuration, a package template; receiving, using the processor, first prescription information including a name of a patient, a name of a medication, a dosage of the medication, an amount of the medication, and a schedule for taking the medication; creating, using the processor, the package template and the first prescription information, a first custom label including a first plurality of data fields including the first prescription information and a first shape and a first size for the first custom label; transmitting, using the processor, first data, including the first custom label with the first prescription information entered in the first plurality of data fields, to a printer; printing, using a printer; the first data on a sheet; and cutting, using a two-dimensional cutter, the sheet to form the label.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Moreover, although any methods, devices or materials similar or equivalent to those described herein can be used in the practice or testing of these embodiments, some embodiments of methods, devices, and materials are now described.

Figure 1:
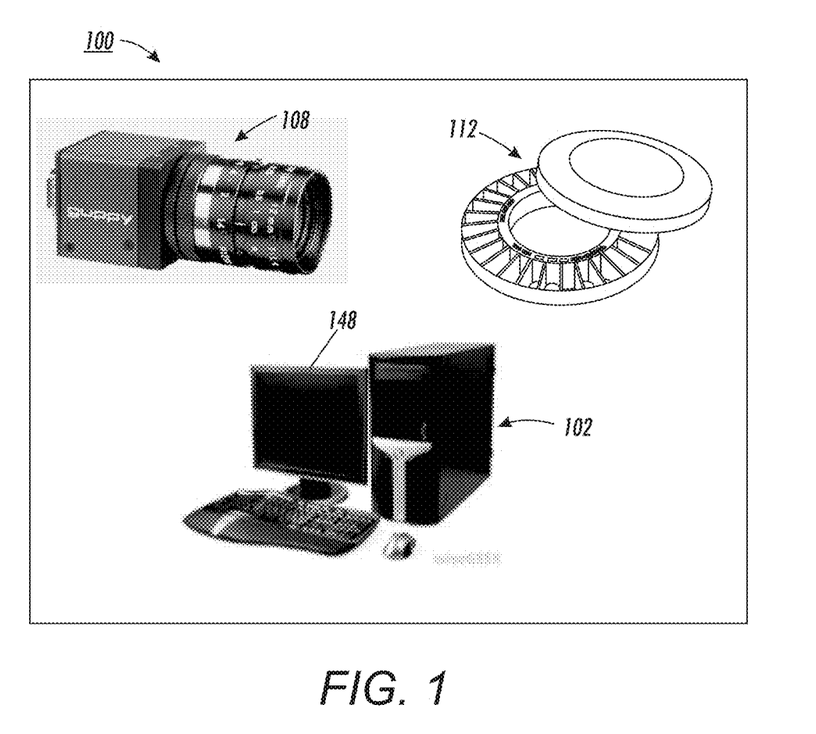
FIG. 1 is a schematic illustration of a computer-based apparatus for labeling medications.

FIG. 1 is a schematic illustration of computer-based apparatus 100 for labeling medications.

Figure 2:
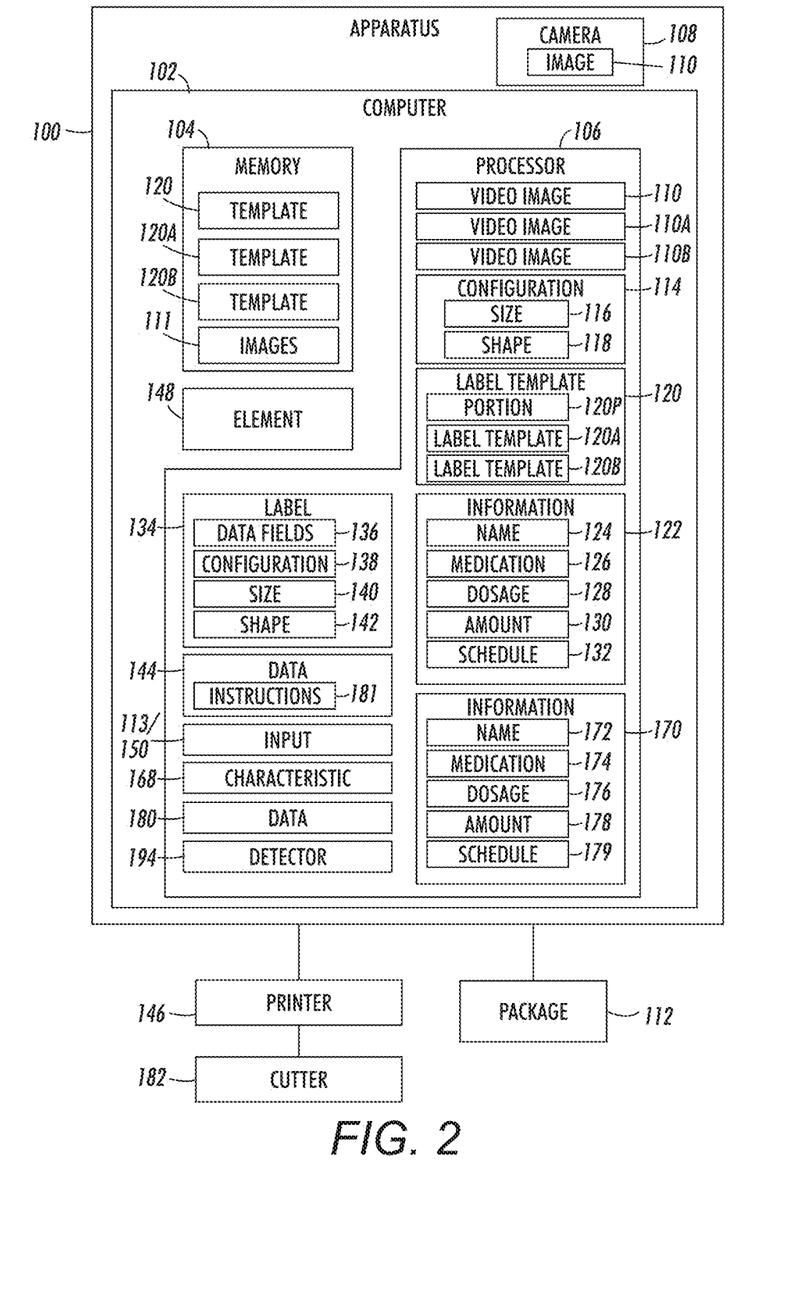
FIG. 2 is a schematic block diagram of the computer-based apparatus shown in FIG. 1.

FIG. 2 is a schematic block diagram of the computer-based apparatus shown in FIG. 1. The following should be viewed in light of FIGS. 1 and 2. Apparatus 100 includes computer 102, with memory element 104 and processor 106 configured to calculate, using digital image 110 of package 112, configuration 114 of medication package 112 and create label template 120 using configuration 112.

By "configuration" of a package we mean a description or representation of the structure of the package, for example, the physical space or surface available for receiving a label. For example, configuration 112 can include two-dimensional data, such as size 116 and shape 118 of the package as a whole or of surfaces of the package. As further described below, a configuration also can include three-dimensional information such as protrusions or recesses on or in a surface which must be accommodated by a label, or surface or textural information such as indicia on a surface that also must be accommodated by a label.

By "template" we mean a digital file representing a label for a medication package and including a plurality of selectable blank data fields and a plurality of designators for the data fields. The data fields are arranged to receive data regarding a patient or medication and can accommodate any indicia known in the art, including but not limited to text, graphics, photographs, and surface features, such as embossed symbols or Braille letters. The size and shape of the template is selectable according to the size and shape of a package, for example using configuration 112, in particular for example, according to the size, shape, and other features of a package surface to which the label is to be attached. The placement, size, and relative positioning of data fields and designators within the template is variable or selectable as needed or desired to fit within the dimensional constraints of label, for example, as derived from configuration 112. The process of selecting and positioning data fields and designators can be done automatically by a computer, by a computer using input from a user, for example, from a person packaging a medication, or by a combination of an automatic computer process and input from the user.

In an example embodiment, processor 106 is configured to receive image 110 from any camera known in the art. In an example embodiment, apparatus 100 includes digital imager, or camera, 108 and camera 108 is configured to create digital image 110 of medication package 112, in an example embodiment, memory 104 is configured to store digital images 111 of medication packages, processor 106 is configured to transmit images 111 for display, and processor 106 is configured to receive input 113 selecting image 110 from images 111. For example, images 111 can include images of generic or commonly used packages.

Processor 106 is configured to receive prescription information 122 including name 124 of a patient, name of medication 126, dosage 128 of medication 126, amount 130 of medication 126, and schedule 132 for taking medication 126. Processor 106 is configured to create custom label 134 including data fields 136, and configuration 138 for label 134. In an example embodiment, configuration 138 includes size 140 and shape 142 for label 134 approximating size 116 and shape 118, respectively. It should be understood that template 118 can accommodate any configuration 114 known in the art. Processor 106 is configured to enter prescription information 122 in data fields 136 and transmit data 144, including label 134 with prescription information 122 entered in data fields 136, to a printer, for example, printer 146.

Figure 3:
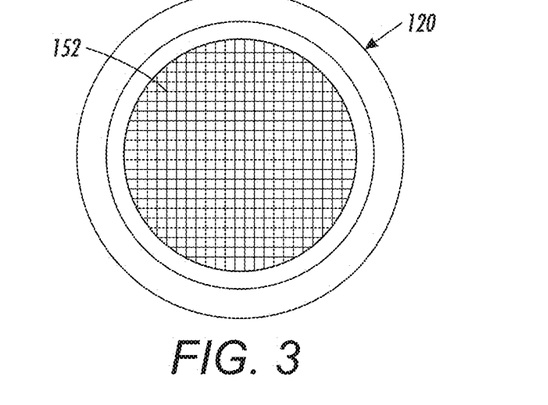
FIG. 3 is a schematic representation of a package template.

FIG. 3 is a schematic representation of package template 120. In an example embodiment, processor 106 is configured to template 120 on graphical user interface element 148 and receive, via element 148, input 150 selecting portion 120P of template 120. Processor 106 is configured to configure label 134 to fit within portion 120P. Thus, a user of apparatus 100 can determine where and how to fit a label on a package.

Figure 4A:
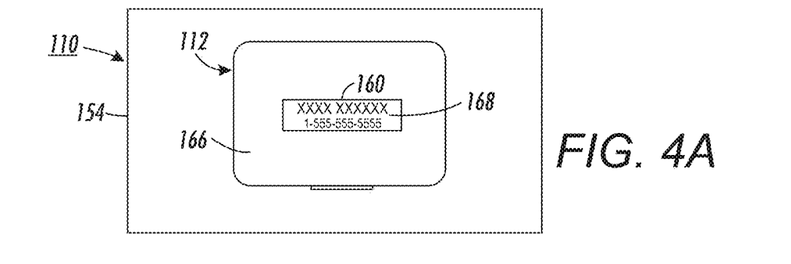
FIG. 4A through 4D show an example sequence of creating a label.
Figure 4B:
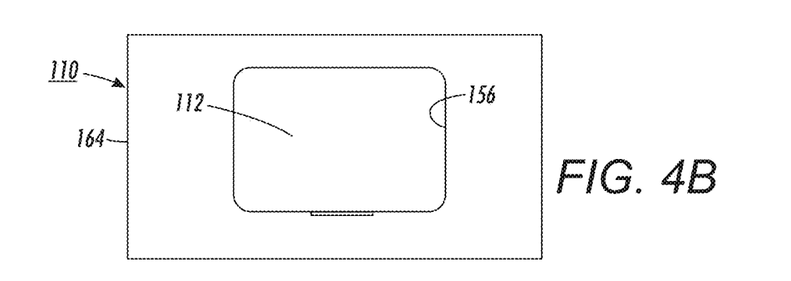
Figure 4C:
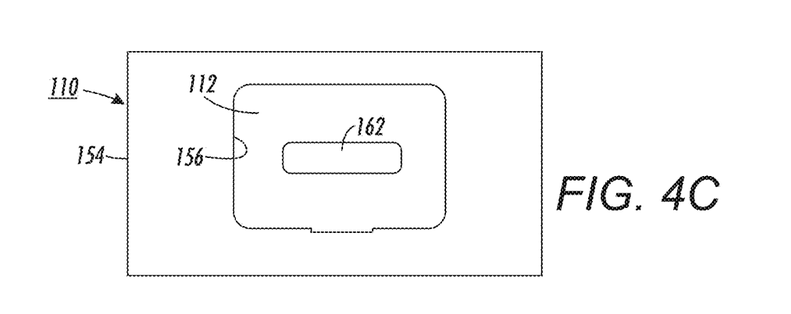
Figure 4D:
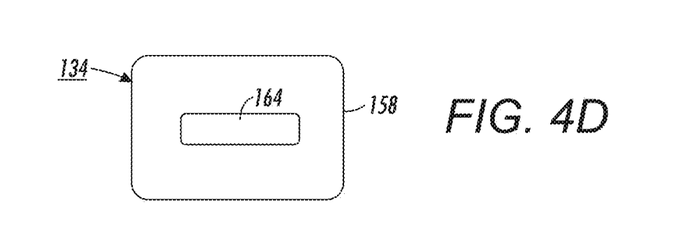

FIGS. 4A thorough 4D show an example sequence of creating a label. In FIG. 4A, digital image 110 shows medication package 112 set against contrasting background 154, for example, a black background. It should be understood that any contrasting background known in the art, for example, zebra stripes, can be used. In FIG. 4B, the processor has generated two-dimensional outline 156 of package 112, for example, using size 116 and shape 118 or portion 120A. In an example embodiment as shown in FIG. 4D, processor 106 is configured to calculate two-dimensional outline 158 of label 134 using configuration 114. In an example embodiment, outline 158 approximates outline 156, for example, outline 158 is substantially the same as outline 156 or fits within outline 156.

In an example embodiment, processor 106 is configured to identify surface variation 160 on medication package 112, for example, within outline 156 or bordering outline 156. In an example embodiment, processor 106 is configured to create cutout 162 for label 134 positioned to coincide with surface variation 160. For example, cutout 162 is removed from the label so that when the label is placed on medication package 112 the surface variation is visible through opening 164 formed when cutout 162 is removed. In an example embodiment, processor 106 is configured to identify surface 166 of medication package 112 and identify surface variation 160 with respect to surface 166, for example, as protruding from surface 166 or recessed with respect to surface 166. For example, in FIG. 4A, variation 160 includes an indented area.

Figure 5:
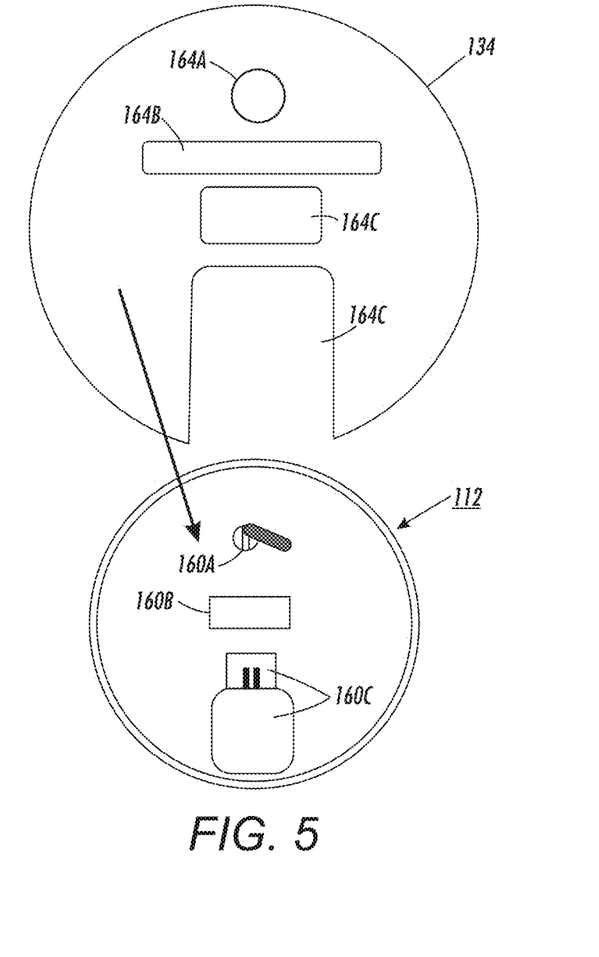
FIG. 5 is a schematic representation of an example medication package and label.

FIG. 5 is a schematic representation of example medication package 112 and example label 134. In FIG. 5, variation 160A is a protrusion, variation 160B is a recess for a display, and variation 160C is a recess for dispensing medications. Cutouts are made in label 134 to create openings 164A, 164B, and 164C to enable access to variations 160A, 160B, and 160C, respectively.

In an example embodiment, processor 106 is configured to identify visual characteristic 168 different from surface 166. In an example embodiment, feature 168 is text or graphics. In an example embodiment, the text or graphics are substantially co-planar with surface 166 or are part of surface 166, for example, printed on surface 166.

It should be understood that the respective discussions for FIGS. 4A through 5 are not limited to the packages shown and are applicable to any type of medication package known in the art.

In an example embodiment, processor 106 is configured to store template 120 in memory element 104. In an example embodiment, camera 108 is configured to create digital image 110A of a particular medication package 112, create template 120A as described above, and store template 120A in memory element 104. At a later time, camera 108 is configured to create digital image 110B of the same medication package 112 or another medication package 112. Processor 106 is configured to compare digital images 110A and 110B to determine that the medication package of image 110B is the package of image 110A or substantially matches the medication package of image 110A. Processor 106 is configured to create template 120B, having substantially configuration 114. Processor 106 is configured to receive prescription information 170 including name 172 of a patient, name of medication 174, dosage 176 of medication 174, amount 178 of medication 174, and schedule 179 for taking medication 174. Processor 106 is configured to enter prescription information 170 in data fields 136 for template 120B and transmit data 180, including label template 120B with prescription information 170 entered in data fields 136, to the printer. It is possible for prescription information 170 to be the same as prescription information 122.

In an example embodiment, data 144 includes instructions 181 for printing, using the printer, prescription information 122 entered in data fields 136 on a sheet, and cutting, using a cutter, for example cutter 182, the sheet to form label 134.

Figure 6A:
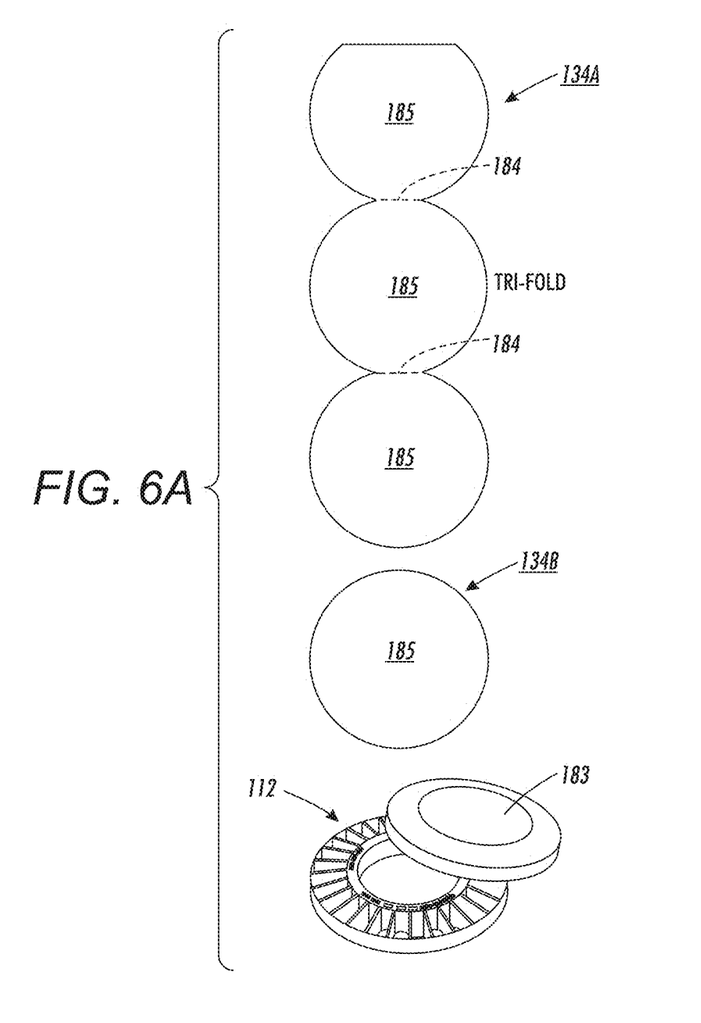
FIGS. 6A thorough 6D illustrate example labels.
Figure 6B:
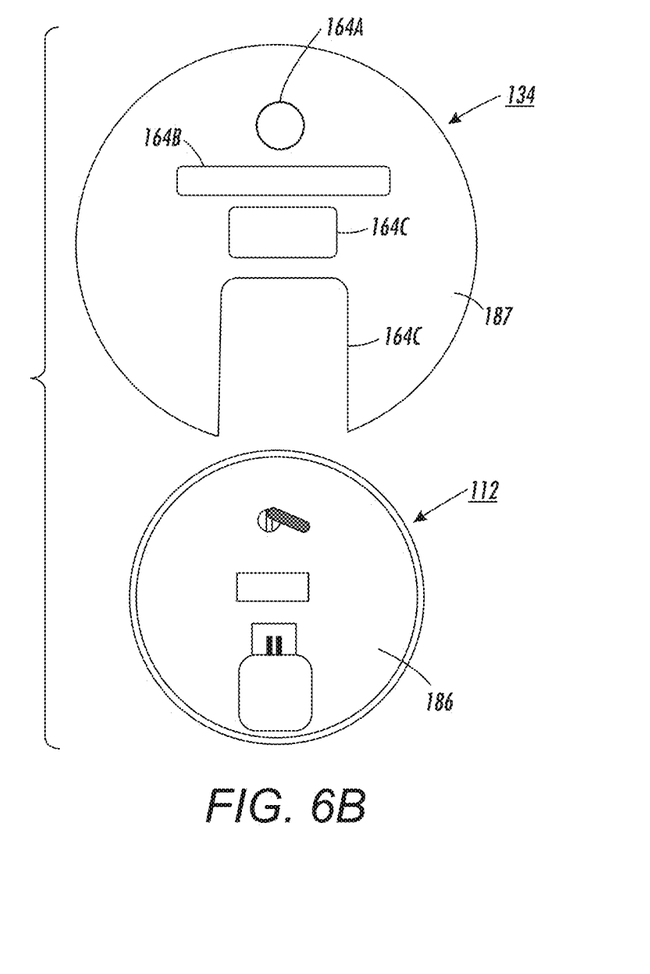
Figure 6C:
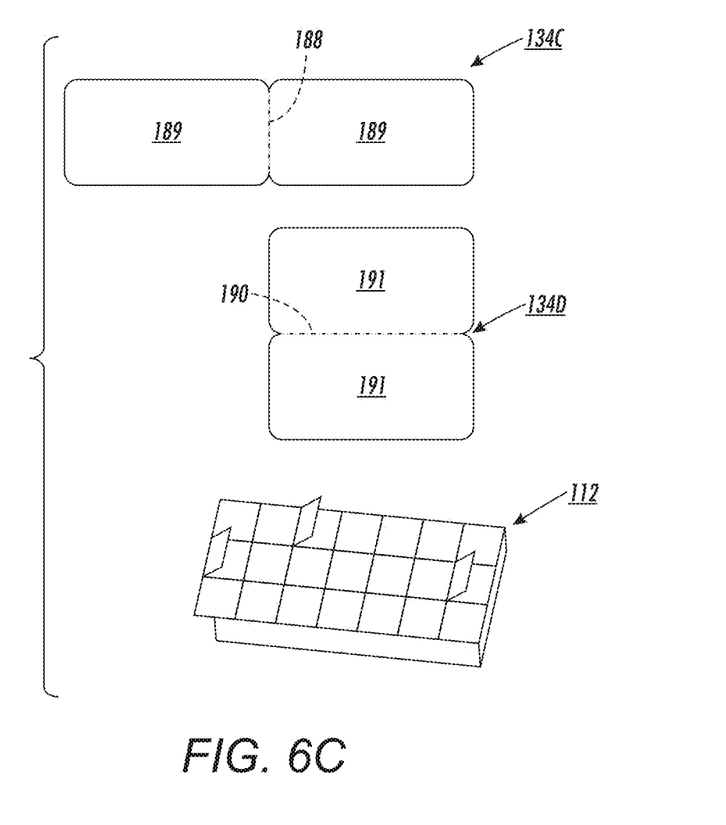
Figure 6D:
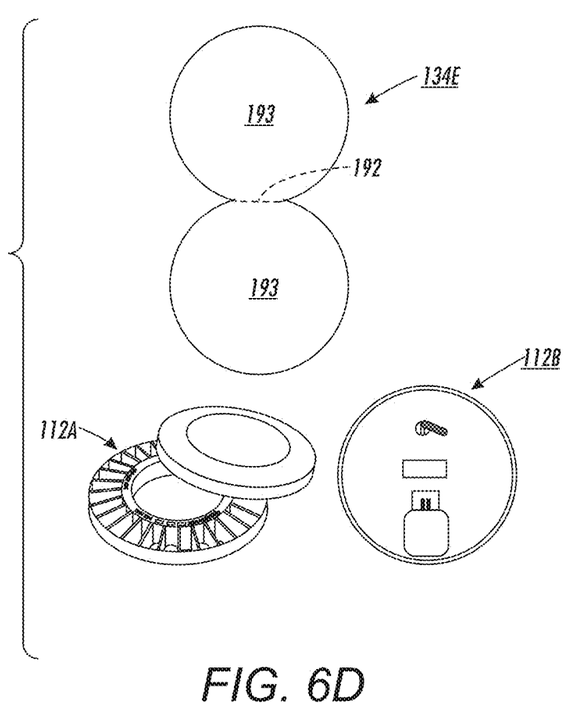

FIGS. 6A thorough 6D illustrate example labels. FIG. 6A illustrates tri-fold label 134A arranged to attachment to front portion 183 of package 112 and single layer label 134B arranged for attachment to a back portion of package 112 not visible in FIG. 6A. Label 134A is foldable at lines 184. The printer is arranged to print information 122 on surfaces 185. In FIG. 6B, label 134 is arranged for attachment to front surface 186 of package 112 and the printer is arranged to print information 122 on surface 187. FIG. 6C illustrates rectangular bi-fold labels 134C and 134D. Label 134C is foldable along line 188 and the printer is arranged to print information 122 on surfaces 189. Label 134D is foldable along line 190 and the printer is arranged to print information 122 on surfaces 191. In the case of FIG. 6C, the labels are arranged to attach to the back of package 112. FIG. 6D illustrates circular bi-fold label 134E. Label 134E is foldable along line 192 and the printer is arranged to print information 122 on surfaces 193. Label 134 is arranged to attach to the front of package 112A or to the back of package 112B. It should be understood that any number and type of folds are possible for labels 134 and that any combination of different types of labels 134 can be applied to different portions of a medication package.

Figure 7:
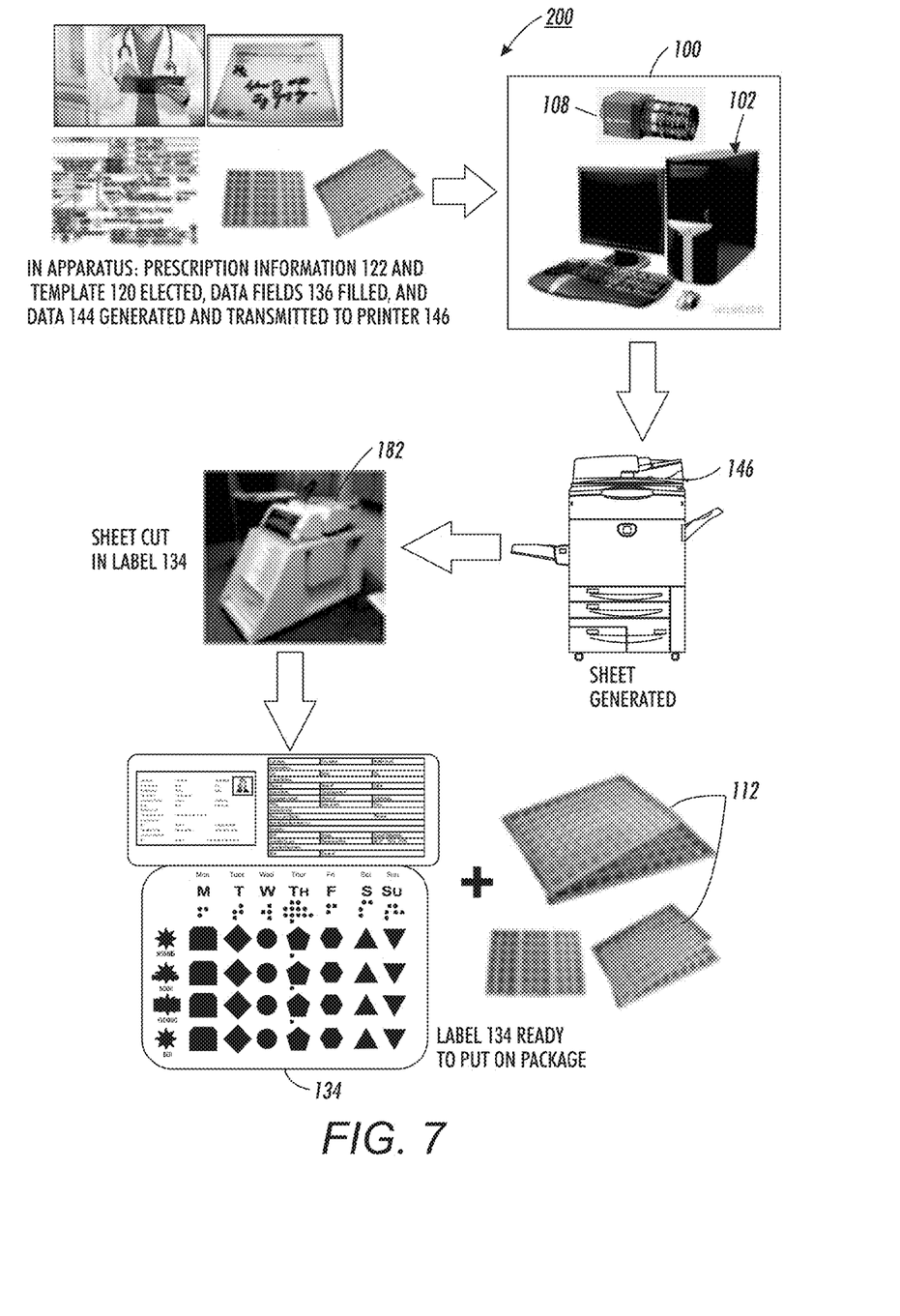
FIG. 7 is a schematic flow chart of an example system including the apparatus of FIG. 1.

FIG. 7 is a schematic flow chart of system 200 including apparatus 100 of FIG. 1. Printer 146 prints a sheet including information 122 and two-dimensional cutter 182 cuts the sheet to form label 134. Printer 146 and cutter 182 can be any printer or cutter, respectively, known in the art.

The discussion that follows is directed to apparatus 100, although is should be understood that the discussion is applicable to system 200 as well. Apparatus 100 enables the flexible functionality described above; that is, the creation of custom-configured labels, at a point of sale or point of distribution, such as a hospital pharmacy or other local pharmacy, and enables the use of any medication package known in the art.

Apparatus 100 integrates digital imaging capability with the functionality of creating or selecting a template to include data fields to accommodate information such as prescription information 122, automatically filling in the data fields with the information, and adding other options such a surface texture features. Thus, entities, such as pharmacies, providing prescription medications to video individual medication packages, provided by the entity or by customers, to create a customized template and package label that prior to the video was not available for use. Then, once the customized template is created, the customized template is saved for later use.

Apparatus 100 can use any digital image and object recognition hardware, firmware, or software known in the art to capture and process a digital image of an individual medication package provided by or given to a pharmacy. In an example embodiment, object recognition software generates template 120 based on the prominent features and textures of the structure of the subject package. Pharmacy personnel select portion 120P of the template suitable for printing and link information, such as information 122, with portion 120P to initiate the transfer of the information to data fields in portion 120P. In an example embodiment, apparatus 100 assigns a unique barcode designation to the template and sends a print file to a standard digital printer, such as printer 146, and the label template file to a two-dimensional cutter, such as cutter 182. For example, a sheet of printed media is loaded into the cutter, which reads the barcode and cuts label 134 from the sheet of media. The pharmacy fills the medication package, and attaches the label. The package is ready for delivery to the customer.

In general, estimating the dimension of a three-dimensional object usually requires 3-D capturing or stereo vision (with multiple cameras). However, in an example embodiment, since many medication packages limited heights, the length and width surface dimensions of the package can be estimated with sufficient accuracy from the images captured by a calibrated normal two-dimensional red/blue/green (RGB) camera. For example, a typical configuration is to mount the camera at the top and place the medication package under the camera on a flat surface. In an example embodiment, the center of the package to be examined is aligned with the optical center line of the camera In an example embodiment, shape recognition from digital image 110 includes an object extraction step and an optional shape classification step. In object extraction, the object, for example, surface 166 is separated from background 154. Any means known in the art, for example, simple thresholding, can be used for extraction. The detected object can be directly used for generating template 120. In an example embodiment, the shape of the object can be further classified into different shape categories (circular, rectangular, etc) and the associated parameters, such as radius for a disk, width and height for a rectangle, are estimated to provide more accurate templates 120. Any means known in the art, for example Hough transform, can be used for extraction and detection.

In an example embodiment, processor 106 includes texture detector 194, which detects surface variations 160, such as buttons, digital displays, or embossed features. For example, detector 194 detects regions whose local variances are greater than a threshold, for example as shown in FIGS. 4A through 4D. FIG. 4A is an image captured by a digital camera. FIG. 4B is the object extracted by background thresholding. FIG. 4C is the embossed printed area extracted by texture detector 194. FIG. 4D is the result of shape and texture recognition, in this case, a rectangle with round corners and center cutout.

In an example workflow, a customer brings a package 112 to a pharmacy. A technician at the pharmacy creates images 110 of the front and back of the package using camera 108 and apparatus 100 generates template 120. The technician or a pharmacist selects portion 120P of the template suitable for printing, in an example embodiment, the technician or pharmacist selects the number and location of folds, such as folds 184, 188, 190 or 192.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A computer-based apparatus for labeling medications, comprising: a processor for a computer configured to: calculate a configuration of a first medication package using a first digital image of the medication package; create, using the configuration, a package template; receive first prescription information including a name of a patient, a name of a medication, a dosage of the medication, an amount of the medication, and a schedule for taking the medication; create a first custom label, using the package template and the first prescription information, the first custom label including: a first plurality of data fields including the first prescription information; and, a configuration for the first custom label; transmit first data, including the first custom label with the first prescription information entered in the first plurality of data fields, to a printer; and, a memory element, wherein the processor is configured to store the package template in the memory element, wherein the processor is further configured to: compare the first digital image with a second digital image of a second medication package to determine that the second medication package substantially matches the first medication package; when the second medication package substantially matches the first medication package: receive second prescription information including a name of a patient, a name of a medication, a dosage of the medication, an amount of the medication, and a schedule for taking the medication; create a second custom label, using the package template and the second prescription information, the second custom label including: a second plurality of data fields including the second prescription information; and, a second configuration for the second custom label; and, transmit second data, including the second custom label with the second prescription information entered in the second plurality of data fields, to the printer.

2. The computer-based apparatus of claim 1, wherein the processor is configured to receive the first digital image of the first medication package.

3. The computer-based apparatus of claim 1, further comprising:
a camera arranged to create the first digital image and transmit the first digital image to the processor.

4. The computer-based apparatus of claim 1, further comprising:
a memory element configured to store a plurality of digital images of medication packages, wherein: the processor is configured to:
transmit the plurality of digital images of medication packages for display; and,
receive an input selecting the first digital image from the plurality of digital images of medication packages.

5. The computer-based apparatus of claim 1, wherein the configuration for the first custom label includes a first shape and a first size for the first custom label.

6. The computer-based apparatus of claim 1, wherein the processor is configured to:
display, using a graphical user interface device, the package template; and,
receive an input selecting a portion of the package template; and,
creating the first custom label includes configuring the first custom label to fit within the portion.

7. The computer-based apparatus of claim 6, wherein:
the processor is configured to calculate a two-dimensional outline of the portion; and,
creating the first custom label includes creating a two-dimensional outline for the first custom label, the two-dimensional outline for the first custom label approximating the outline of the first medication package.

8. The computer-based apparatus of claim 1, wherein the processor is configured to:
display the package template;
receive an input selecting a shape for the first custom label; and,
create the first custom label to match the shape.

9. The computer-based apparatus of claim 1, wherein calculating a configuration of the first medication package includes calculating a size and a shape of at least one surface of the first medication package.

10. The computer-based apparatus of claim 1, wherein:
the processor is configured to identify:
a surface of the first medication package; and,
a surface variation, with respect to the surface, of the first medication package; and,
creating the first custom label includes creating a cutout for the custom label, the cutout positioned to coincide with the surface feature.

11. The computer-based apparatus of claim 10, wherein:
the surface variation protrudes from the surface or is recessed with respect to the surface; or,
the surface variation includes a first visual characteristic different from a second visual characteristic of the surface.

12. The computer-based apparatus of claim 11, wherein the first visual characteristic includes text or graphics on the surface.

13. The computer-based apparatus of claim 1, wherein the first data includes instructions for:
printing, using the printer, the first prescription information entered in the first plurality of data fields on a sheet; and,
cutting, using a cutter, the sheet to form the label.

14. A computer-based system for labeling medications, comprising: a printer; a two-dimensional cutter; and, a processor for a computer configured to: calculate a configuration of a first medication package using a first digital image of the first medication package; create, using the configuration, a package template; receive first prescription information including a name of a patient, a name of a medication, a dosage of the medication, an amount of the medication, and a schedule for taking the medication; create a first custom label, using the package template and the first prescription information, the first custom label including: a first plurality of data fields including the first prescription information; and, a first shape and a first size for the first custom label; transmit first data, including the first custom label with the first prescription information entered in the first plurality of data fields, to a printer; compare the first digital image with a second digital image of a second medication package to determine that the second medication package substantially matches the first medication package; when the second medication package substantially matches the first medication package: receive second prescription information including a name of a patient, a name of a medication, a dosage of the medication, an amount of the medication, and a schedule for taking the medication; create a second custom label, using the package template and the second prescription information, the second custom label including: a second plurality of data fields including the second prescription information; and, a second shape and a second size for the second custom label; and, transmit second data, including the second custom label with the second prescription information entered in the second plurality of data fields, to the printer, wherein: the printer is configured to print the first data on a first sheet and the second data on a second sheet; and, the two-dimensional cutter is configured to cut the first sheet to form the first custom label and the second sheet to form the second custom label.

15. The computer-based system of claim 14, wherein the processor is configured to receive the first digital image of the first medication package.

16. The computer-based system of claim 14, further comprising:
a camera arranged to create the first digital image and transmit the first digital image to the processor.

17. The computer-based system of claim 14, further comprising:
a memory element configured to store a plurality of digital images of medication packages, wherein: the processor is configured to:
transmit the plurality of digital images of medication packages for display; and,
receive an input selecting the first digital image from the plurality of digital images of medication packages.

18. The computer-based system of claim 14, wherein the processor is configured to:
display, using a graphical user interface device, the package template; and,
receive an input selecting a portion of the package template; and,
creating the first custom label includes configuring the first custom label to fit within the portion.

19. The computer-based system of claim 14, wherein:
the processor is configured to identify:
a surface of the first medication package; and,
a surface variation, with respect to the surface, of the first medication package; and,
creating the first custom label includes creating a cutout for the custom label, the cutout positioned to coincide with the surface feature.

20. A computer-based method for labeling medications, comprising: calculating, using the processor, a configuration of the first medication package using a first digital image of a first medication package; creating, using the processor and the configuration, a package template; receiving, using the processor, first prescription information including a name of a patient, a name of a medication, a dosage of the medication, an amount of the medication, and a schedule for taking the medication; creating, using the processor, the package template and the first prescription information, a first custom label including: a first plurality of data fields including the first prescription information; and, a first configuration for the first custom label; transmitting, using the processor, first data, including the first custom label with the first prescription information entered in the first plurality of data fields, to a printer; comparing, using the processor, the first digital image with a second digital image of a second medication package to determine that the second medication package substantially matches the first medication package; when the second medication package substantially matches the first medication package: receiving, using the processor, second prescription information including a name of a patient, a name of a medication, a dosage of the medication, an amount of the medication, and a schedule for taking the medication; creating, using the processor, a second custom label, using the package template and the second prescription information, the second custom label including: a second plurality of data fields including the second prescription information; and, a second configuration for the second custom label; and, transmitting, using the processor, second data, including the second custom label with the second prescription information entered in the second plurality of data fields, to the printer.

21. The computer-based method of claim 20, further comprising:
receiving, using the processor, is the first digital image of the first medication package.

22. The computer-based method of claim 20, further comprising:
creating, using a camera the first digital image; and,
transmitting, using the camera, the first digital image to the processor.

23. The computer-based method of claim 20, further comprising:
storing, in a memory element, a plurality of digital images of medication packages;
transmitting, using the processor, the plurality of digital images of medication packages for display; and,
receiving, using the processor, an input selecting the first digital image from the plurality of digital images of medication packages.

24. The computer-based method of claim 20, wherein the configuration for the first custom label includes a first shape and a first size for the first custom label.

25. The computer-based method of claim 20, further comprising:
displaying, using the processor and a graphical user interface device, the package template; and,
receiving, using the processor, an input selecting a portion of the package template, wherein creating the first custom label includes configuring the first custom label to fit within the portion.

26. The computer-based method of claim 20, further comprising:
calculating, using the processor, a two-dimensional outline of the portion, wherein creating the first custom label includes creating a two-dimensional outline for the first custom label, the two-dimensional outline for the first custom label approximating the outline of the first medication package.

27. The computer-based method of claim 20, further comprising:
displaying, using the processor, the package template;
receiving, using the processor, an input selecting a shape for the first custom label; and, creating, using the processor, the first custom label to match the shape.

28. The computer-based method of claim 20, further comprising:
identifying, using the processor, a surface of the first medication package; and,
identifying, using the processor, a surface variation, with respect to the surface, of the first medication package; and,
creating the first custom label includes creating a cutout for the custom label, the cutout positioned to coincide with the surface feature.

29. The computer-based method of claim 20, further comprising:
storing, using the processor, the template in a memory element.

30. The computer-based method of claim 20, further comprising:
including in the first data, using the processor, instructions for:
printing, using the printer, the first prescription information entered in the plurality of data fields on a sheet; and,
cutting, using a cutter, the sheet to form the first custom label.

31. A computer-based method for labeling medications, comprising: calculating, using a processor, a configuration of a first medication package using a first digital image of the first medication package; creating, using the processor and the configuration, a package template; receiving, using the processor, first prescription information including a name of a patient, a name of a medication, a dosage of the medication, an amount of the medication, and a schedule for taking the medication; creating, using the processor, the package template and the first prescription information, a first custom label including: a first plurality of data fields including the first prescription information; and, a first shape and a first size for the first custom label; transmitting, using the processor, first data, including the first custom label with the first prescription information entered in the first plurality of data fields, to a printer; printing, using a printer, the first data on a sheet; cutting, using a two-dimensional cutter, the sheet to form the label; comparing, using the processor, the first digital image with a second digital image of a second medication package to determine that the second medication package substantially matches the first medication package; when the second medication package substantially matches the first medication package: receiving, using the processor, second prescription information including a name of a patient, a name of a medication, a dosage of the medication, an amount of the medication, and a schedule for taking the medication; creating, using the processor, a second custom label, using the package template and the second prescription information, the second custom label including: a second plurality of data fields including the second prescription information; and, a second shape and a second size for the second custom label; and, transmitting, using the processor, second data, including the second custom label with the second prescription information entered in the second plurality of data fields, to the printer.

32. The computer-based method of claim 31, further comprising:
receiving, using the processor, the first digital image of the first medication package.

33. The computer-based method of claim 31, further comprising: creating, using a camera, the first digital image; and, transmitting, using the camera, the first digital image to the processor.

34. The computer-based method of claim 31, further comprising:
storing, in a memory element, a plurality of digital images of medication packages;
transmitting, using the processor, the plurality of digital images of medication packages for display; and,
receiving, using the processor, an input selecting the first digital image from the plurality of digital images of medication packages.

35. The computer-based method of claim 31, further comprising:
displaying, using the processor and a graphical user interface device, the package template; and,
receiving, using the processor, an input selecting a portion of the package template, wherein creating the first custom label includes configuring the first custom label to fit within the portion.

36. The computer-based method of claim 31, further comprising:
displaying, using the processor, the package template;
receiving, using the processor, an input selecting a shape for the first custom label; and,
creating, using the processor, the first custom label to match the shape.

37. The computer-based method of claim 31, further comprising:
identifying, using the processor, a surface of the first medication package; and,
identifying, using the processor, a surface variation, with respect to the surface, of the first medication package; and,
creating the first custom label includes creating a cutout for the custom label, the cutout positioned to coincide with the surface feature.

38. The computer-based method of claim 31, further comprising:
storing, using the processor, the template in a memory element.

39. The computer-based method of claim 31, further comprising:
including in the first data, using the processor, instructions for:
printing, using the printer, the first prescription information entered in the plurality of data fields on a sheet; and,
cutting, using a cutter, the sheet to form the first custom label.

* * * * *